(12) United States Patent
Aughenbaugh

(10) Patent No.: US 8,927,824 B2
(45) Date of Patent: *Jan. 6, 2015

(54) HYBRID TOMATO 'ESAS'

(71) Applicant: Ernest S. Aughenbaugh, St. Johns, MI (US)

(72) Inventor: Ernest S. Aughenbaugh, St. Johns, MI (US)

( * ) Notice: Subject to any disclaimer, the term of this patent is extended or adjusted under 35 U.S.C. 154(b) by 22 days.

This patent is subject to a terminal disclaimer.

(21) Appl. No.: 13/975,296

(22) Filed: Aug. 24, 2013

(65) Prior Publication Data

US 2014/0059723 A1 Feb. 27, 2014

Related U.S. Application Data

(63) Continuation of application No. 12/932,523, filed on Feb. 28, 2011, now Pat. No. Plant 24,181.

(51) Int. Cl.
*A01H 5/00* (2006.01)
*C12N 5/04* (2006.01)
*A01G 1/00* (2006.01)
*A01H 5/08* (2006.01)

(52) U.S. Cl.
CPC . *A01G 1/001* (2013.01); *A01H 5/08* (2013.01)
USPC .............. 800/317.4; 800/317.1; 435/411; 435/423; 47/58.1 FV

(58) Field of Classification Search
CPC .... A01H 5/08; C07K 14/415; C12N 15/8261; A01G 9/00
USPC ............. Plt./261; 800/317.4, 317.1; 435/411, 435/423; 47/58.1 FV See application file for complete search history.

(56) References Cited

U.S. PATENT DOCUMENTS

| | | |
|---|---|---|
| PP4,539 P | 5/1980 | Briggs |
| PP5,171 P | 1/1984 | Briggs |
| PP5,812 P | 11/1986 | Pezzulla |
| 7,807,886 B2 | 10/2010 | Fowler |

*Primary Examiner* — June Hwu
(74) *Attorney, Agent, or Firm* — Technology Law PLLC; Karen L. Kimble

(57) ABSTRACT

A new and distinct variety of paste-type hybrid tomato plant is described that is derived in part from an Amish tomato, and in part from a Big Bertha Pepper. This hybrid tomato has 2-4 lobes similar to a pepper, a hardy skin, and remains on the vine when ripe until frost. When picked ripe, this tomato lasts longer without rotting than normal tomatoes. Some of these tomatoes have been eaten after 3 months from picking. The fruit usually shrinks inside itself after some time from picking.

7 Claims, 6 Drawing Sheets

HYBRID TOMATO 'ESAS'

CROSS REFERENCE TO RELATED APPLICATION

This application is a continuation of U.S. Ser. No. 12/932,523, filed Feb. 28, 2011.

BACKGROUND OF THE INVENTION

1. Field of Invention

A new hybrid of paste-type tomato plant has been developed as described and illustrated herein.

LATIN NAME OF THE GENUS AND SPECIES OF THE PLANT CLAIMED

*Solanum lycopersicum*

BACKGROUND OF THE INVENTION

The present plant is a new and distinct tomato plant which was a selection taken from plants found in a cultivated area and then asexually reproduced. The cultivated area was my garden of about 40 feet by 80 feet where tomatoes, peppers, onions, squash, beans, peas, beets, kohlrabi, turnips and other vegetables as desired are grown. The new hybrid was found in one of the rows of vegetables where it was not tiled under. Seeds were grown out and division of the plant done where the plant part (e.g. the stem) was directly planted into the soil without any pretreatment or root growth hormone added. The plant stem formed roots and produced fruit. Selection was based on the shape of the fruit and the hardy skin. Selected seed was again grown out and planted near Amish tomato plants. Selection was again made using the same criteria. This was repeated three times. Selection from the last named generation was based on shape, hearty skin, and ability to remain on the vine after ripened.

2. Description of Parent

Amish tomato, the seed parent, can be both indeterminate and determinate, and is a member of the Roma family. They are disease resistant to fusarium wilt and verticillum. The Amish tomato is a medium size fruit and a usual shape for the Roma family with a rounded or pointed end. The usual Amish tomato is shown in some of the photographs provided with this application.

Big Bertha Pepper, the pollen parent, is a green pepper and has no use as a tomato. As with most peppers, this tomato has characteristics of definite lobes, internal ridges, and retention on the plant after ripened.

BRIEF SUMMARY OF THE INVENTION

This invention relates to a new paste-type hybrid tomato that is distinguished from both of its parents. This new tomato plant (named Tulip Tomato™) is also distinguished from other tomato varieties of which I am aware by virtues of several characteristics described herein, especially by its shape and hardy skin.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

The accompanying photographs show a number of specimens of the hybrid plant and its fruit throughout various stages of growth as experienced in the summer of 2010 in central Michigan. The plants were only watered by natural rainfall for the entire growing season.

DETAILED BONTANICAL DESCRIPTION OF THE PLANT

Figure 1:
FIG. 1 is a photograph of the present Tulip Tomato as growing on the vine and showing the clustering of the tomatoes as they grow.

A detailed description of my new hybrid tomato is as follows—based upon my observation made from plants grown for about seven years in Michigan. The following outline sets forth a number of distinguishing features of this hybrid tomato over plants known before as seen in the photographs of the plant as attached hereto. The color specifications mentioned herein were determined by the reference to Federal Color Standard 595 revision B (FED-STD-595B).

Some of These Plant Characteristics are as Follows:

Type: Paste—type tomato of indeterminate habit bearing a unique shaped fruit having 1-4 lobes with seed cavities corresponding to the number of lobes and a hardy skin. The pointed lobe has 4 divisions and can be seen on the surface of the tomato, and has 4 seed cavities. The seeds are distributed as usual in a tomato and not as found in a pepper.

Breeding: Developed initially by accidental cross-breeding of an Amish tomato (seed parent) and Big Bertha Pepper (pollen parent) varieties and found in a cultivated area, and thereafter by deliberate selecting the most desirable characteristics of the next generation plants. The resulting plant holds its distinguishing characteristics through succeeding propagations by division of the plant (such as taking the stem without roots and directly planting in soil without any pretreatment).

Seed parent: Amish tomato plant.

Pollen parent: Big Bertha Pepper plant.

Propagation: Selection was made from initial found plants in a cultivated area that were grown out and further selections over seven years made based on shape and hardy skin. The present hybrid plant is a selection taken from the plants grown from seeds of the last generation and divisions of the plants by taking stems and planting them. The seed plants and the division plants produce the same fruit having the 1 to 4 lobes and the hardy skin.

Plant

Habit: Indeterminate in growth habit, is hardy and may be used as a ground or staked variety. The stalk is thinner as compared to an Amish tomato. The foliage is relative sparse and about the same color (FS 34110) as the Amish tomato but the green (FS 34110) of the foliage is lighter than the Big Bertha Pepper. The plant reaches maturity in 75 to 90 days after transplanting depending on seasonal conditions. The fruit remains on the vine after being ripe for long periods of time (similar to a green pepper). This enables later picking of the ripe fruit to market as it does not readily fall to the ground soon after being ripe as do other tomato varieties.

Growth: Medium size plant around 5 feet with an average rate of growth. The plants begin to blossom early in the season as the ground warms. Individual blossoms of this hybrid plant are typical of other tomato plants such as five petal and star shaped.

Foliage:

The plants are vine like and can be staked or not. There are numerous branches. The branches coming off the main stalk are close to the ground, and are about 1 to 4 inches apart. Additional leaf stalks and nodes grow on the branches.

Size of leaf: (mature) Leaves are 6 to 7 cm×4 cm and look the same as the Amish tomato variety. The leaves are shown in FIG. 1.

Color: Medium green. (FS 34110)

Main Stems: 132 to 137 cm long. (Tall)

Branches: 8 to 10 branches from the main stem.

New shoots: Up to 22 or more.

Fruit:

Fruit: about 100 to 196 fruit from one plant is obtained in a season until frost. The fruit grows as clusters of about 7 to 13 fruits on a branch, similar to cherry tomatoes. FIG. 1 illustrates this property.

Figure 2:
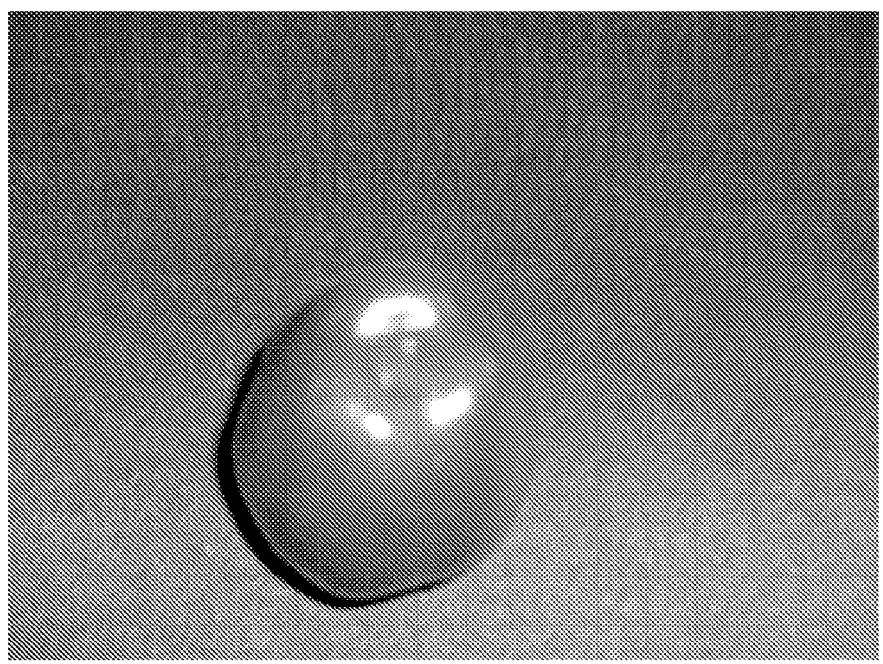
FIG. 2 is a photograph of a 3 lobe Tulip Tomato.

Shape: Similar to a green pepper or apple shape having 2 to 4 lobes all having definite division of sections similar to a green pepper. The lobes can be observed on the outside of the tomato and has internal seed cavities corresponding to the number of lobes, except the pointed or 1 lobe variety which has 4 seed cavities. FIG. 2 shows a 3 lobe Tulip Tomato.

Figure 3:
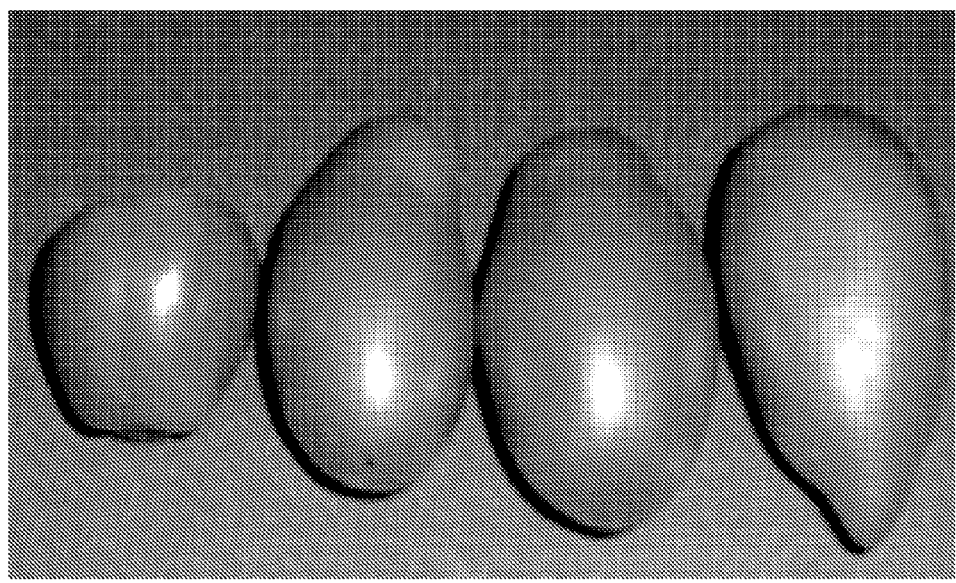
FIG. 3 is a photograph—from left to right—Tulip Tomato, Roma tomato, Roma tomato, and Amish tomato.
Figure 4:
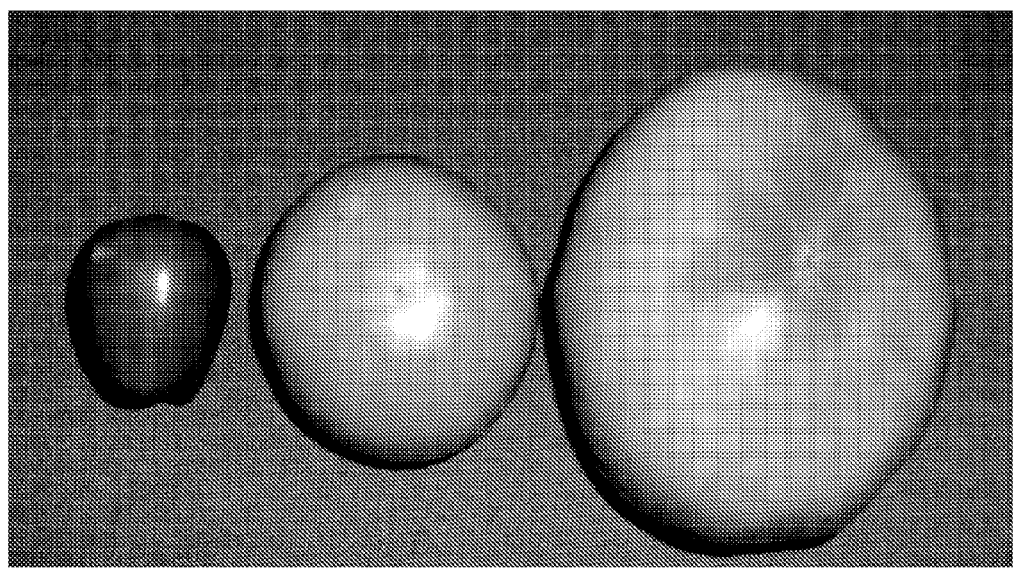
FIG. 4 is a photograph—from left to right—Tulip Tomato, Golden Girl tomato, and Mr. Stripey tomato.
Figure 5:
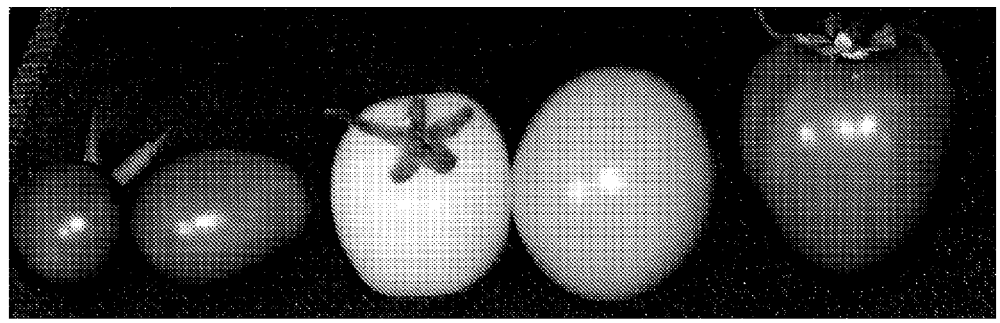
FIG. 5 is a photograph—from left to right—Cherry tomato, Grape tomato, Italian Ice, large yellow grape tomato, and Tulip tomato.

Size: Average weight is about 15.75 to 27.45 grams, about 3.2 to 4 cm in width, and 3.7 to 4 cm in height. Thus this Tulip Tomato is larger than a cherry tomato but smaller than its Amish tomato parent. See FIGS. 3, 4 and 5 showing these size differences.

Texture: Firm. The skin is hardy like a green pepper and the number of lobes represents the number of seed cavities, except the pointed or 1 lobe variety which has 4 seed cavities.

Color (skin): Immature—light green (FS 33814) face with waxy appearance and often with a darker green (FS 34109) shoulder. Mature—light red (FS 33120) to red (FS 31128).

Color (flesh): light red (FS 33120) to red (FS 31128).

Bearing Season: The bearing season is from 75 to 90 days after transplanting, and the plant will hold most fruit until frost (if the weather cooperates).

Flavor: mild tomato taste/meaty with low acid.

Skin: the skin is quite tough, and similar to a green pepper.

Figure 6:
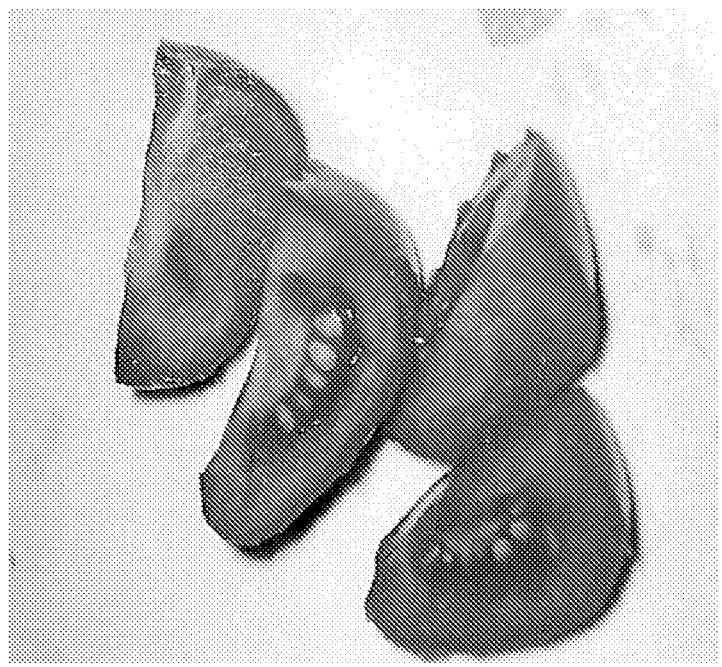
FIG. 6 is a photograph of a Tulip Tomato cut open about 60 days after being picked and showing that it is still firm inside, with no visible deterioration but some wrinkling on the outer skin.

Disease resistance: similar to the Amish tomato resistance to fusarium wilts and verticillum—with the only insects seen being the tomato cut worm and grasshoppers. Fruit flies only happen if the fruit is damaged. If the fruit is not damaged, this hybrid resists rotting very well for long periods of time and the usual white fungus does not appear. After picking a ripe fruit, the fruit will shrink inside itself over time, like the pepper, but can still be safely eaten months after picking. FIG. 6 shows a Tulip Tomato after about 60 days from picking having these stated characteristics. (Note: I have taken the seeds out of the tomato after 8 months and eaten the pulp. Taste is about the same as the usual fruit at picking.) Not all Tulip Tomatoes will last this long, but frequently do last on an average about 30 days or more.

Use: as a paste—type tomato for human consumption with likely ease of mechanical picking as it remains on the vine after ripening until frost.

Bearing Qualities:

Quality: The plants have been grown for the last 7 years with the above qualities appearing every season and are shown fixed in the asexual reproduction of the plant.

This new hybrid is improved over its parents in that it displays certain properties of each of its parents but improves on the resulting fruit. The Tulip Tomato advantages over its parents are: 1) it has a hardy skin, 2) usually 2-4 lobes for its shape, 3) its size is larger than a cherry tomato and smaller than a Roma tomato or Amish tomato, and 4) it remains on the vine until frost after ripening.

DEPOSIT INFORMATION: A deposit of the hybrid tomato "Esas", disclosed above, and recited in the claims, will be made not later than upon allowance of the application and before, payment of the issue fee with the American Type Culture Collection (ATCC) Patent Depository, 10801 University Blvd., Manassas, Va. 20110. The dates of deposits are Sep. 25, 2014. The accession numbers for those deposited seeds are ATCC No PTA-121619. Upon issuance of a patent, all restrictions on the availability to the public of the deposits will be irrevocably removed, and the deposits are intended to meet all the requirements of 37 C.F.R. §1.801-§1.809. The deposits will be maintained in the depository for a period of 3.0 years, or 5 years after the last request, or for the enforceable life of the patent, whichever is longer, and will be replaced if necessary during that period.

I claim:

1. A seed of hybrid tomato 'Esas', a sample of seed of said hybrid having been deposited under ATCC Accession Number PTA-121619.

2. A tomato plant or part thereof produced by growing the seed of claim 1.

3. A tomato fruit of the plant of claim 2.

4. The tomato fruit of claim 3, wherein the fruit has from 1 to 4 lobes with seeds in the lobes if 2, 3 or 4 lobes and if 1 lobe then 4 seed cavities, and a hardy skin like a green pepper.

5. The tomato fruit of claim 3, wherein if the fruit is not damaged resists rotting for at least 30 days.

6. The plant part of claim 2, further defined as a leaf, an ovule, pollen, a fruit, or a cell.

7. A method of sexually propagating a tomato plant comprising:

a) collecting seed from the fruit of tomato hybrid 'Esas', representative seed of said hybrid having been deposited under ATCC Accession Number PTA-121619;

b) planting such seed to obtain a plantlet;

c) growing a plant from such plantlet; and d) obtaining the fruit from the plant.

* * * * *